(12) United States Patent
Rotundo

(10) Patent No.: US 8,354,379 B2
(45) Date of Patent: Jan. 15, 2013

(54) PEPTIDES THAT ENHANCE ACETYLCHOLINESTERASE EXPRESSION

(75) Inventor: Richard L. Rotundo, Miami, FL (US)

(73) Assignee: University of Miami, Miami, FL (US)

( * ) Notice: Subject to any disclaimer, the term of this patent is extended or adjusted under 35 U.S.C. 154(b) by 652 days.

(21) Appl. No.: 12/514,384

(22) PCT Filed: Aug. 14, 2007

(86) PCT No.: PCT/US2007/017950

§ 371 (c)(1), (2), (4) Date: Jan. 13, 2010

(87) PCT Pub. No.: WO2008/088385

PCT Pub. Date: Jul. 24, 2008

(65) Prior Publication Data

US 2011/0183922 A1    Jul. 28, 2011

Related U.S. Application Data

(60) Provisional application No. 60/837,315, filed on Aug. 14, 2006.

(51) Int. Cl.
*A61K 38/00* (2006.01)
*A61K 38/10* (2006.01)

(52) U.S. Cl. ...................................... 514/21.5; 530/326

(58) Field of Classification Search .................. None
See application file for complete search history.

(56) References Cited

FOREIGN PATENT DOCUMENTS

WO    WO 2004015396 A2 *  2/2004

OTHER PUBLICATIONS

Luo et. al. Calcineurin enhances Acetycholinesterase mRNA Stability during C2-C'1 Muscle Cell Differentiation, Molecular Pharmacology, vol. 56, 886-894 (1999).*
Curtin et. al (Histone Acetylase Inhibitor Trichostatin A Induces Acetylcholinesterase Expression and Protects Against Organophosphate exposure, Journal of Cellular Biochemistry 96: 839-849, 2005).*
(Histone Acetylase Inhibitor Trichostatin A Induces Acetylcholinesterase Expression and Protects' Against Organophosphate Exposure, Journal of Cellular Chemistry 96: 839-849, 2005) *Reference already in prosecution history.*
Belbeoc'h et al. The C-Terminal T Peptide of Acetylcholinesterase Enhances Degradation of Unassembled Active Subunits Through the ERAD Pathway, The EMBO Journal. Jul. 15, 2003, vol. 22, Nov. 14, pp. 3536-3545.

* cited by examiner

*Primary Examiner* — Christina Bradley
*Assistant Examiner* — Jeanette Lieb
(74) *Attorney, Agent, or Firm* — Novak Druce + Quigg LLP

(57) ABSTRACT

The present invention provides novel chimeric peptides and novel methods for treating animals including humans by administering the novel chimeric peptides. In particular, the invention is useful for enhancing endogenous acetylcholinesterase expression in individuals exposed to organophosphate compounds, such as nerve gases and pesticides.

24 Claims, 8 Drawing Sheets

US 8,354,379 B2

PEPTIDES THAT ENHANCE ACETYLCHOLINESTERASE EXPRESSION

CROSS REFERENCE TO PRIOR APPLICATIONS

This is a U.S. National Phase application under 35 U.S.C. §371 of International Patent Application No. PCT/US2007/017950, filed Aug. 14, 2007, and claims the benefit of U.S. Provisional Application No. 60/837,315, filed Aug. 14, 2006, both of which are incorporated by reference herein. The International Application published in English on Jul. 24, 2008 as WO 2008/088385 under PCT Article 21(2).

GOVERNMENT SUPPORT

Work described herein may have been supported in part by NIH Grant number R01 AG05917 from the National Institute on Aging (NIA) and U01-NS057994 from National Institute of Neurological Disorders and Stroke (NINDS). The U.S. Government may have certain rights in the invention.

FIELD OF THE INVENTION

The present invention is directed generally to the field of cell biology. More particularly, the present invention provides novel chimeric peptides and novel methods for treating animals including humans by administering the novel chimeric peptides.

BACKGROUND OF THE INVENTION

Since the introduction of biological and chemical weapons during the First World War, intensive research and development by the super power nations has led to the creation of large stockpiles of chemical weapons and new technologies for the delivery of these weapons. These weapons of mass destruction are so named because of their ability to kill enormous numbers of people in a short period. Weapons of this nature are attractive to both developing countries and terrorist groups because they are easier and cheaper to acquire than nuclear weapons. Moreover, the technologies and synthetic methodologies for manufacturing some chemical weapons are openly available and easily accessible to the public. Terrorists may seek to obtain greater status or bargaining power against their more developed enemies by demonstrating that they have the technological capabilities required to develop, produce, and deliver chemical and biological warfare agents.

Although the use of biological and chemical weapons is banned by international treaty, these weapons are thought to be in the stockpiles of several extremist nations and terrorist organizations. The release of the nerve gas sarin in the Tokyo subway system in 1995, killing 12 and wounding over 1000, demonstrated the consequences of chemical warfare technology in the hands of terrorists and/or anarchists. In the United States, the threat and fear of potential terrorist attacks using biological and chemical weapons has been particularly elevated since the attacks of Sep. 11, 2001.

Nerve gases, such as sarin, soman, tabun, and VX, are classified chemically as organophosphate compounds. Organophosphates are characterized as stable, easily dispersed, and highly toxic, with toxicity taking effect rapidly both when absorbed through the skin and via respiration. The threat of organophosphate poisoning is not limited to exposure to nerve gases, as commercial pesticides such as malathion and parathion are also organophosphate compounds that are toxic upon exposure. In the United States, approximately 20,000 reported organophosphate exposures occur per year; however, it is estimated that only 1% of field worker illness from pesticide exposure is reported. Internationally, organophosphate poisoning occurs in virtually every country in the world. The United Nations reports that over 30,000 organophosphate-related fatalities occur worldwide each year. Third world countries have less legislation regarding safe agricultural use of pesticides; therefore, a much higher incidence of poisoning exists among field workers and the public who buy produce from these fields.

Organophosphate compounds inactivate cholinesterases, including acetylcholinesterase (AChE) and butyrylcholinesterase (BuChE), by phosphorylating the active site serine hydroxyl group on the enzyme, leading to the loss of ability to hydrolyze the substrate acetylcholine. AChE is the enzyme that terminates neurotransmission at the neuromuscular synapse. The normal function of cholinergic synapses requires that the neurotransmitter acetylcholine (ACh) be hydrolyzed by cholinesterases within several milliseconds to terminate neurotransmission. Organophosphate poisoning occurs when the inactivated enzyme is unable to break down ACh, leading to ACh accumulation throughout the autonomic nervous system, the somatic nervous system, and the brain, resulting in overstimulation of the acetylcholine receptors. Prolongation of neurotransmission results in extensive damage to the target cells and, frequently, death of the organism. Decreasing muscle strength leading to paralysis occurs when motor plates remain depolarized by persisting levels of acetylcholine. The inhibition of AChE by nerve gases generally results in death by asphyxiation within a few minutes, as control is lost over respiratory muscles.

AChE is highly concentrated at sites of nerve-muscle contact where it is attached to the specialized basal lamina juxtaposed between the nerve terminal and the postsynaptic membrane (reviewed in Massoulié et al., 1993; Legay, 2000; Rotundo, 2003). The only known function of AChE at the synapse is to rapidly hydrolyze the neurotransmitter acetylcholine thus terminating neurotransmission. The high concentration of AChE between the nerve terminal and the muscle membrane is maintained primarily by the muscle, and the newly synthesized AChE molecules are released into the synaptic cleft.

All AChE forms in vertebrates are encoded by a single gene and, in mammals, give rise by alternative splicing to one to three polypeptide chains of about 480 amino acids depending on the species. Birds appear to express only one variant, of higher apparent kDa, whereas most mammals express at least two alternatively spliced forms. All forms share the same catalytic domain containing about 95% of the total sequence, however the H form ($AChE_h$) has a 30-40 amino acid carboxyl terminus that is cleaved post-translationally and a glycophosphoinositol (GPI) anchor covalently attached, whereas the T form ($AChE_t$) that has a different 40 amino acid terminus that allows assembly with one of two non-catalytic subunits specifying subcellular localization (FIG. 1). The GPI-anchored form is expressed only in hematopoietic and lymphatopoietic tissues where its function is unknown. In addition to the catalytic subunits, there are two non-catalytic subunits encoded by separate genes that associate with the enzyme to target it to specific regions of the cell surface, the collagenic tail (ColQ) and the transmembrane anchoring "p" peptide or PRIMA (reviewed in Massoulié et al. 1993; Legay, 2000; Rotundo, 2003).

Only the $AChE_t$ form is expressed in nerves and muscle in most vertebrates. The major forms of AChE expressed in neurons are monomers and dimers and in particular the tetrameric form covalently linked to the small transmembrane PRIMA peptide that anchors it to the plasma membrane. The minor forms are intracellular or secreted and appear to be a precursor pool in the secretory pathway, the endoplasmic reticulum and the Golgi apparatus. In skeletal muscle, the major forms are the soluble globular and collagen-tailed versions of AChE with little or no expression of other variants (FIG. 1). The most important form is the collagen-tailed AChE that is the predominant, if not unique, form at the neuromuscular synapse. The inactivation of this form at the neuromuscular junction of the diaphragm is usually the proximal cause of death.

The appearance of collagen-tailed AChE forms is dependent upon expression of the collagenic tail itself, ColQ (FIG. 2). The ColQ is encoded by a separate gene and is expressed in many tissues including skeletal muscle. The ColQ molecule is composed of several distinct functional domains including the N-terminal domain (NTD) that associates covalently via SH bonds with the catalytic subunits, the triple-helical collagenic domain, and the C-terminal domain (CTD) responsible for anchoring the ColQ AChE to the synaptic basal lamina in skeletal muscle. Within the N-terminal domain is the 17 amino acid PRAD sequence, the Proline-Rich Attachment Domain (Bon et al., 1997). Analysis of the N-terminal domain showed that this region is responsible for the covalent attachment of the catalytic subunits to the ColQ (Bon and Massoulié, 1997; Bon et al., 1997), and moreover, that co-expression in COS cells with the catalytic subunit resulted in increased formation of tetramers from dimers (Bon et al., 1997). Similar observations were made using the mouse muscle C2/C12 cell line (Legay et al., 1999). In fact, the PRAD peptide can even induce assembly of the tetrameric AChE from dimers in solution (Chitlaru et al., 2001). A model for the molecular interactions responsible for this association based on the crystal structure of the complex has been presented recently (Dvir et al., 2004). Similar to ColQ, the transmembrane anchoring "p" peptide (PRIMA) also comprises a PRAD sequence within its N-terminal domain that can induce tetramerization of AChE.

Current strategies for treatment of individuals exposed to organophosphate compounds include reactivation of inactivated AChE using oxime reactivators, prophylactic administration of muscarinic antagonists such as atropine, and placement of the victim on a ventilator if necessary. Oxime reactivators such as 2-pyridine aldoxime methiodide (2-PAM) restore the function of inactivated AChE by displacing the covalently bound organophosphate molecule from the inactivated enzyme. However, poisoning by some nerve agents, such as soman, is complicated by the inhibited enzyme going through an "aging" process (Strayer reaction) that renders it incapable of being reactivated by any oxime. Atropine binds to muscarinic acetylcholine receptors to protect against excess acetylcholine-mediated neurotransmission resulting from AChE inhibition. However, atropine treatment has no direct effects on the inactivated AChE, the nerve gas, or on nicotinic acetylcholine receptors. In cases of severe nerve gas poisoning, large doses of atropine need to be taken until the level of functional AChE is restored. Moreover, in spite of ongoing developments in these types of treatments, the fatality rate could remain as high as 35% with large-scale exposure during a military conflict.

Another strategy employed to reduce the deadly effects of nerve gas exposure is to pretreat individuals at risk of exposure to organophosphate compounds with active site antagonists such as pyridostygmine bromide (PB). However, this strategy has its own harmful drawbacks. PB is a carbamate compound that is thought to protect AChE by reversibly binding to ("carbamylating") it, so that the nerve agent cannot bind to it. It may also assist in protection against nerve agent by "desensitizing" ACh receptors. However, PB treatment may lead to bromide intoxication from prolonged consumption of excessive doses of bromide, causing protean symptoms, particularly psychiatric, cognitive, neurological, and dermatologic (and some believe this may be the cause of the "Gulf War Syndrome").

The most current research efforts to reduce the effects of exposure to nerve agents that inhibit AChE focus on the development of scavenging enzymes that stoichiometrically inactivate the nerve agent, or catalytic scavenging enzymes capable of hydrolyzing nerve agents in situ, in both cases reducing the effectiveness of the nerve agent. To this end, various forms of recombinant AChE, butyrylcholinesterase, paraoxonase, and other enzymes have been developed and studied for their effectiveness (Broomfield et al., 1991; Allon et al., 1998; Billeck et al., 1999; Broomfield et al., 1999; Saxena et al., 1997; 1998). However, at best these molecules would be administered systemically and would inactivate unreacted organophosphates but leave untouched the inactivated AChE molecules. Thus there still remains little that can be done for victims that have been exposed to high levels of organophosphates.

Conventional methods of treatment for victims of nerve agent or pesticide poisoning are thus limited to controlling the damage caused by nerve agent exposure and/or limited in effectiveness only with certain organophosphate compounds. Moreover, the costs associated with such treatments are not limited to the financial costs required to deliver massive doses of the drugs in cases of severe poisoning but also include the costs to individuals suffering from deleterious side effects resulting from treatment.

There is a need for a method of treating organophosphate poisoning that directly increases active AChE molecules. There is also a need for a more cost effective and efficacious treatment for nerve agent exposure. The invention is directed to these and other important ends.

SUMMARY OF THE INVENTION

The invention provides novel chimeric polypeptides and methods for the treatment of victims exposed to organophosphate compounds by activating existing but inactive enzyme molecules present in the target tissues. The inactive enzyme molecules activated by the polypeptides of the invention include cholinesterases, such as acetylcholinesterase and butyrylcholinesterase.

In some aspects of the invention, the chimeric polypeptide comprises a polypeptide capable of enhancing endogenous acetylcholinesterase expression. In some embodiments, the polypeptide capable of enhancing endogenous acetylcholinesterase expression is derived from an acetylcholinesterase collagenic tail peptide. In some embodiments, the polypeptide capable of enhancing endogenous acetylcholinesterase expression is derived from an acetylcholinesterase transmembrane anchor protein. In further embodiments, the polypeptide capable of enhancing endogenous acetylcholinesterase expression has an amino acid sequence comprising SEQ ID NO:1 or SEQ ID NO:2.

In some embodiments, the chimeric polypeptide further comprises an endoplasmic retention signal. In further embodiments, the endoplasmic retention signal has an amino acid sequence comprising SEQ ID NO:3.

In some embodiments, the chimeric polypeptide further comprises a signal for conjugating a label. In further embodiments, the label is fluorescent.

In some embodiments, the chimeric polypeptide comprises an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

The invention also provides a pharmaceutical composition comprising the chimeric polypeptide and a pharmaceutically acceptable carrier, excipient, or diluent.

The invention further provides a method of treating an animal exposed to an organophosphate comprising enhancing endogenous acetylcholinesterase expression. In some embodiments, the method comprises administering to the animal a therapeutically effective amount of a chimeric polypeptide of the invention. In some embodiments, the method comprises administering to the animal a therapeutically effective amount of a pharmaceutical composition of the invention. In further embodiments, the therapeutically effective amount of the chimeric polypeptide or pharmaceutical composition may be administered parenterally, intravenously, intramuscularly, subcutaneously, or intraperitoneally. The organophosphate may be a nerve gas, such as sarin, soman, tabun and VX, or a pesticide, such as malathion, parathion, diazinon, fenthion, dichlorvos, and chlorpyrifos.

The invention also provides a method of enhancing endogenous acetylcholinesterase expression in an animal in need thereof. In some embodiments, the method comprises administering to the animal a therapeutically effective amount of a chimeric polypeptide of the invention. In some embodiments, the method comprises administering to the animal a therapeutically effective amount of a pharmaceutical composition of the invention. In further embodiments, the therapeutically effective amount of the chimeric polypeptide or pharmaceutical composition may be administered parenterally, intravenously, intramuscularly, subcutaneously, or intraperitoneally.

Other aspects of the invention are directed to a kit for treating organophosphate poisoning comprising a therapeutically effective amount of a chimeric polypeptide or pharmaceutical composition of the invention.

DETAILED DESCRIPTION

Figure 1:
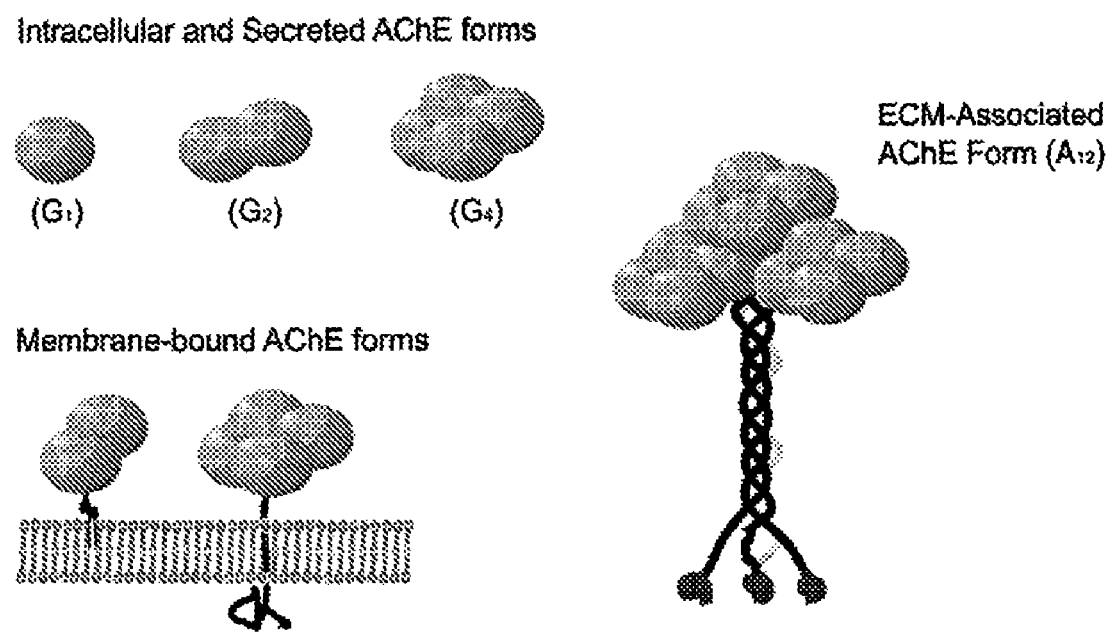
FIG. 1 illustrates the oligomeric forms of AChE in animals. The major secretable forms of AChE consist of monomers ($G_1$), dimers ($G_2$), and tetramers ($G_4$) of the AChE catalytic subunit. The collagen-tailed (ColQ) synaptic form of AChE ($A_{12}$) attaches to the extracellular matrix (ECM) at the synapse. The G series are the lobular forms, and the membrane-bound forms are the GPI-anchored and the PRIMA-associated.
Figure 2:
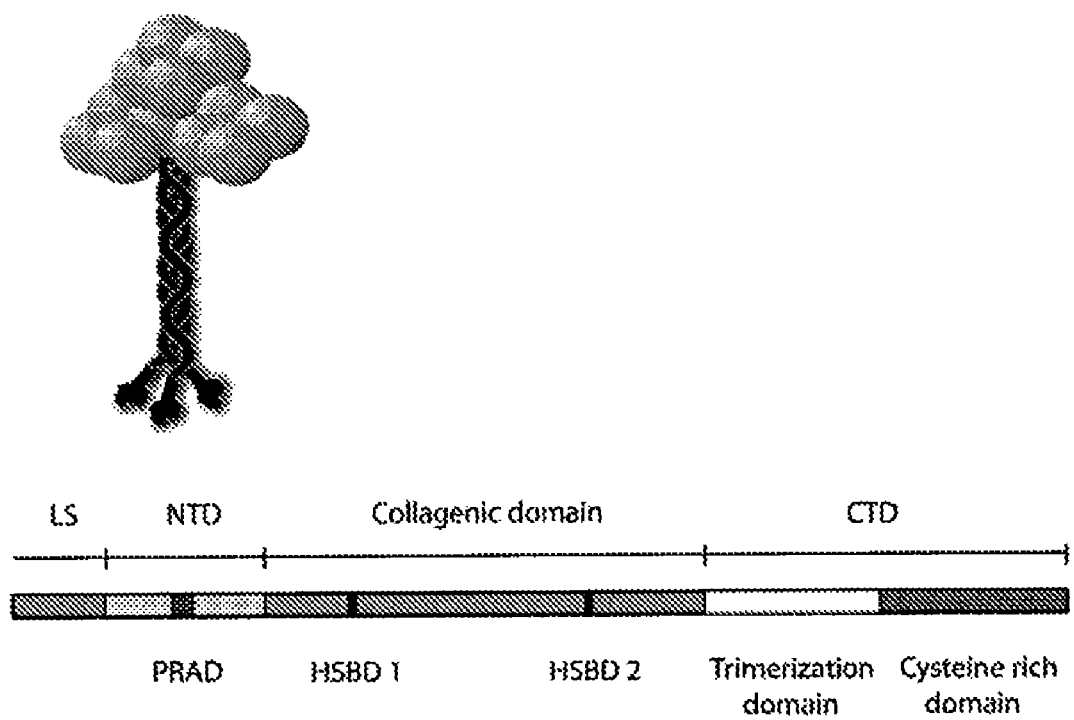
FIG. 2 illustrates the structure of the functional AChE form present at the neuromuscular junction and the organization of a collagenic tail (ColQ) polypeptide chain. Following the leader sequence (LS), the N-terminal domain (NTD) of the ColQ chain contains a proline-rich attachment domain (PRAD) responsible for attachment of the tetrameric forms of the AChE catalytic subunit. The collagenic domain contains two heparin sulfate binding domains (HSBD 1 and HSBD 2). The C-terminal domain (CTD) of the ColQ chain contains a trimerization domain and a cysteine rich domain.

For the purposes of promoting an understanding of the principles of the invention, reference will now be made to specific embodiment and specific language will be used to describe the same. It will nevertheless be understood that no limitation of the scope of the invention is thereby intended, such alteration and further modifications of the invention, and such further applications of the principles of the invention as illustrated herein, being contemplated as would normally occur to one skilled in the art to which the invention relates.

All terms as used herein are defined according to the ordinary meanings they have acquired in the art. Such definitions can be found in any technical dictionary or reference known to the skilled artisan, such as the *McGraw-Hill Dictionary of Scientific and Technical Terms* (McGraw-Hill, Inc.), *Molecular Cloning: A Laboratory Manual* (Cold Spring Harbor, N.Y.), and *Remington's Pharmaceutical Sciences* (Mack Publishing, PA). These references, along with those references and patents cited herein are hereby incorporated by reference in their entirety.

The invention provides novel chimeric polypeptides and methods for the treatment of victims exposed to organophosphate compounds by activating newly-synthesized but inactive enzyme molecules or by stabilizing existing ones present in the target tissues. The inactive enzyme molecules activated by the polypeptides of the invention include cholinesterases, such as acetylcholinesterase and butyrylcholinesterase.

In some aspects, the invention is directed to novel chimeric polypeptides capable of enhancing endogenous acetylcholinesterase (AChE) expression and novel methods of treating organophosphate poisoning that involve enhancing endogenous AChE expression. "Organophosphates" refer to compounds capable of inactivating cholinesterases by phosphorylating the serine hydroxyl group located on the active site of the enzyme. Phosphorylation inactivates the enzyme when a covalent bond forms between the organophosphate molecule and the enzyme molecule. Exemplary organophosphates include insecticides such as malathion, parathion, diazinon, fenthion, dichlorvos, and chlorpyrifos and nerve gases such as soman, sarin, tabun, and VX.

In accordance with the invention, the novel chimeric polypeptides comprise a polypeptide capable of enhancing endogenous AChE expression. "Enhancing" refers to an increase in expression of endogenous AChE. Any polypeptide that is capable of enhancing AChE expression is within the scope of the invention. For example, the polypeptide may be derived from an acetylcholinesterase collagenic tail peptide, such as the ColQ PRAD peptide. In some embodiments, the polypeptide comprises a ColQ PRAD peptide having an amino acid sequence of CCLLTPPPPPLFPPPFF (SEQ ID NO:1). As another example, the polypeptide may be derived from an acetylcholinesterase transmembrane anchor protein, such as the PRIMA peptide. In some embodiments, the polypeptide comprises a PRIMA PRAD peptide having an amino acid sequence of RPPPPLPPPPLPPPPPR (SEQ ID NO:2). In yet other embodiments, the polypeptide capable of enhancing endogenous AChE expression comprises a proline-rich amino acid sequence.

While studying the early events in AChE synthesis, the inventors surprisingly discovered that about 80% of the newly-synthesized AChE molecules were catalytically inactive and subsequently degraded by the endoplasmic reticulum degradation pathway (ERAD) (Rotundo, 1988; Rotundo, et al. 1989). More recently, while studying the assembly of the multimeric enzyme, it was discovered that the noncatalytic subunit appears to "rescue" the catalytic subunits from degradation and, moreover, stabilizes the tetramers for subsequent transport to the muscle cell surface and secretion. Without wishing to be bound by any particular theory, polypeptides that stabilize the newly-synthesized AChE may enhance endogenous AChE expression by enhancing the folding of the nascent polypeptide chain, stabilizing the newly synthesized AChE polypeptide, and/or by inhibition of intracellular degradation.

In some embodiments, the invention provides peptides that can mimic the ability of the non-catalytic subunits to rescue the enzyme and thereby increase endogenous levels of active AChE. The inventive peptides were designed so that additional sequences can be added to the basic peptide that allow it to be labeled with markers, such as fluorescent tags, in order to localize it to intracellular sites of AChE synthesis and processing. The inventive peptides were shown to be taken up by the cells and transported to the endoplasmic reticulum where they can promote assembly and/or stabilization of AChE. This treatment stimulated a 100-300% increase in the expression of exportable tetrameric enzyme. The peptides were also designed so that an endoplasmic reticulum (ER) retention signal can be added to the basic peptide. ER retention signals are well known to the skilled artisan and are described in, for example, Lotish et al., *Molecular Cell Biology*, 5th ed. (W.H. Freeman, 2003). In some embodiments, an ER retention signal comprising an amino acid sequence of KDEL (SEQ ID NO:3) may be comprised in the polypeptides of the invention.

In accordance with the invention, novel chimeric peptides comprising amino acid sequences selected from the group consisting of CCLLTPPPPPLFPPPFFKDEL (SEQ ID NO:4), KKCCLLTPPPPPLFPPPFFKDEL (SEQ ID NO:5), VNKCCLLTPPPPPLFPPPFFKDEL (SEQ ID NO:6), CCLLTPPPPPLFPPPFFTETKDEL (SEQ ID NO:7), VNKCCLLTPPPPPLFPPPFFTETLDEL (SEQ ID NO:8), KRSVNKCCLLTPPPPPLFPPPFFKDEL (SEQ ID NO:9), CCLLTPPPPPLFPPPFFTETNILKDEL (SEQ ID NO:10), KRSVNKCCLLTPPPPPLFPPPFFTETNILKDEL (SEQ ID NO:11), and RPPPPLPPPPLPPPPPRKDEL (SEQ ID NO:12).

Figure 3:
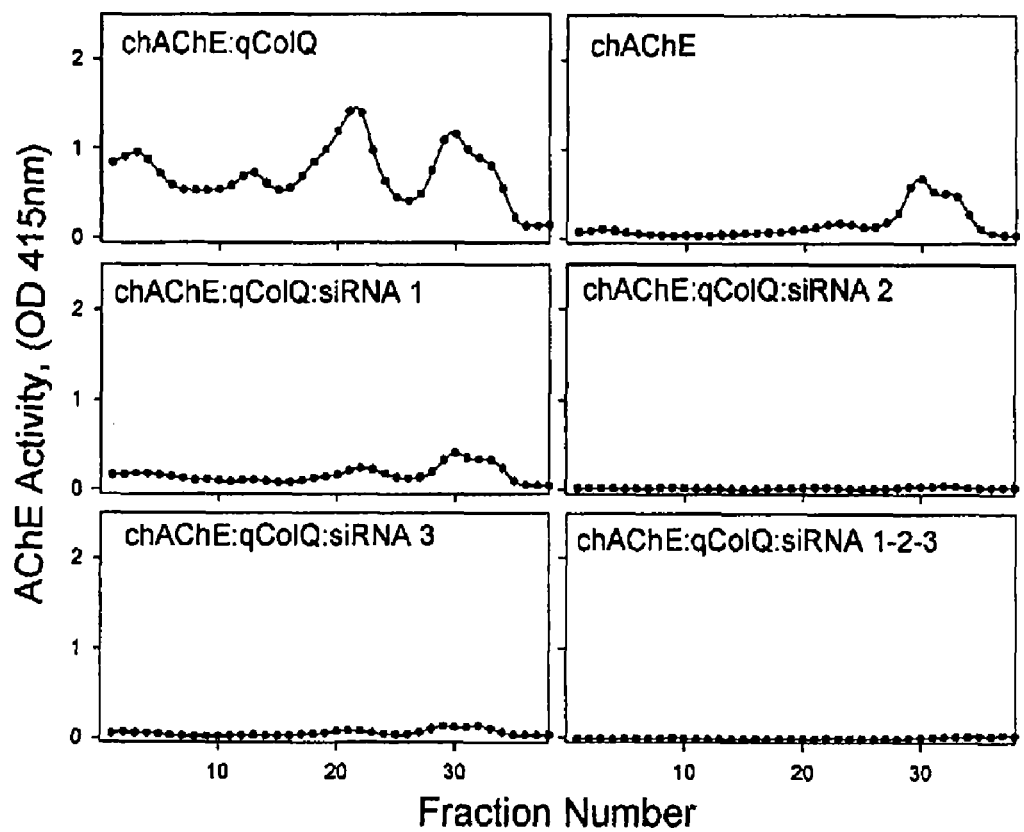
FIG. 3 illustrates the inhibition of qColQ expression by siRNAs in culture. QM7 quail muscle cells were transfected with a plasmid encoding chicken AChE (chAChE) with or without a plasmid encoding quail ColQ (qColQ). ColQ rescues the avian AChE catalytic subunit (upper panels). Co-expression with another plasmid expressing one of three shR-NAs against Col, or all three together, knocks down expression of both the ColQ and the AChE catalytic subunit. The enzyme forms are, from right to left, G2/G1, the G4 tetramer and the collagen tailed forms towards to bottom of the gradient.
Figure 4:
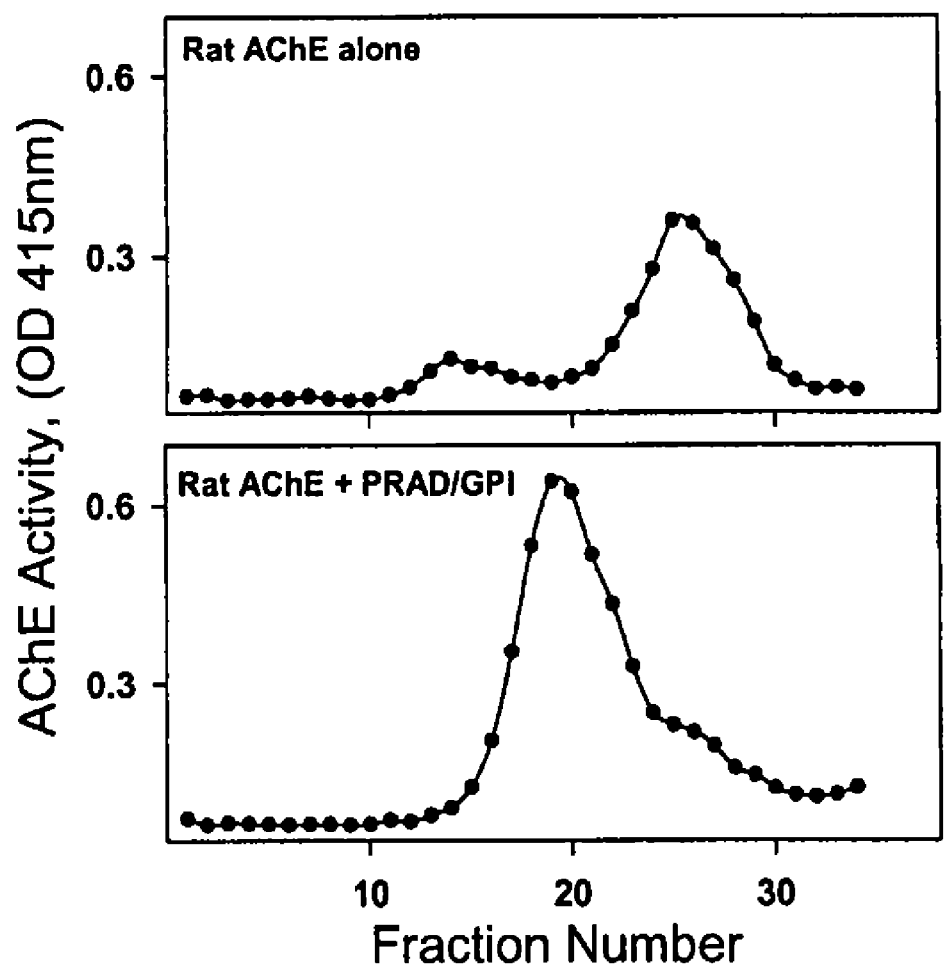
FIG. 4 illustrates the expression of rat AChE in COS cell alone or together with the ColQ PRAD/GPI non-catalytic subunit. The presence of the non-catalytic subunit induces tetramerization and an almost 100% increase in the levels of cell-associated AChE activity. The binding of detergents to the hydrophobic GPI anchor results in a shift in the apparent S value of the tetramer to lighter fractions.
Figure 5:
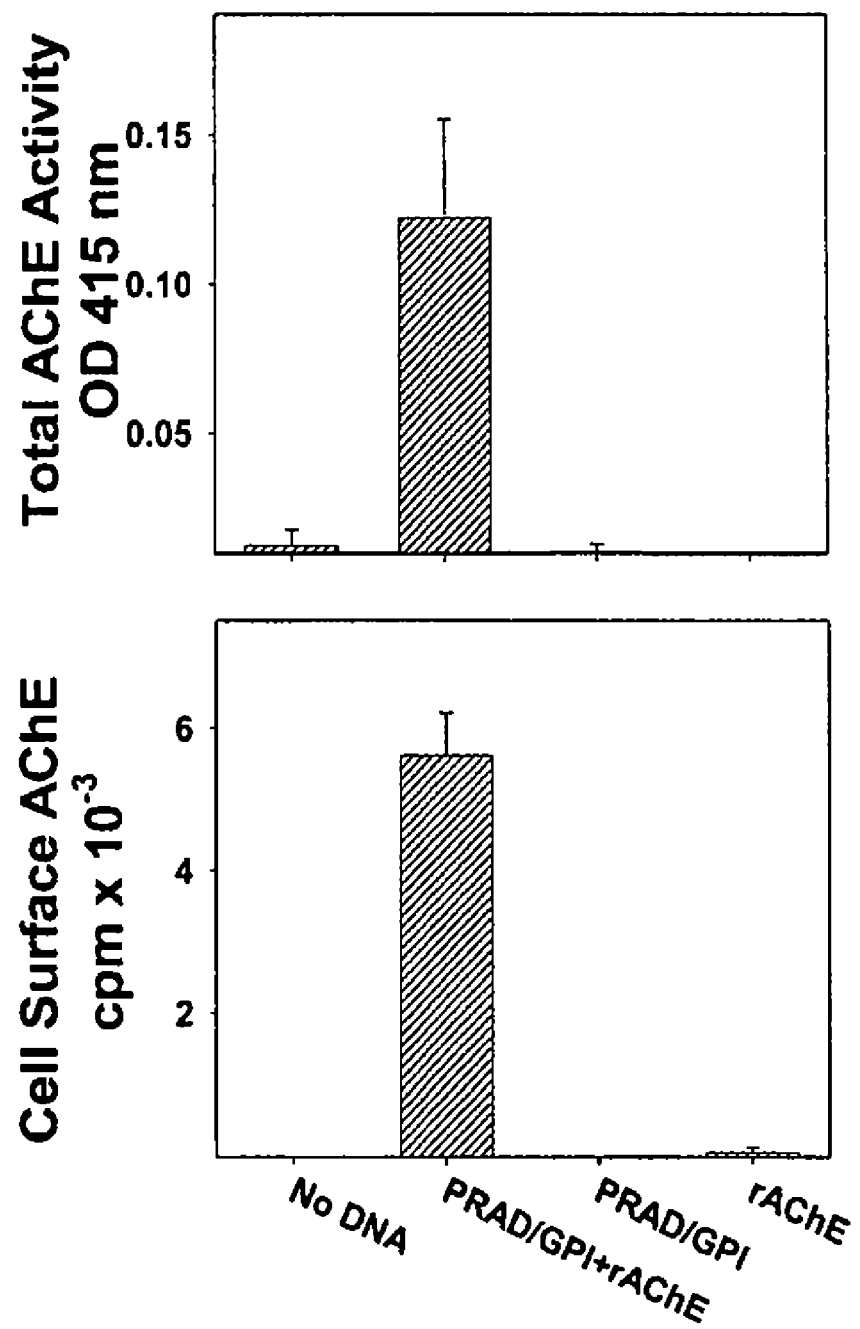
FIG. 5 illustrates the expression of rat AChE and ColQ PRAD-GPI in NIH 3T3 cells. (A) shows total cell AChE activity measured using the Ellman colorimetric assay in transfected and non-transfected cells. (B) shows measurement of cell surface AChE activity using the radiometric cell surface assay. The ColQ PRAD-GPI targeting subunit also rescues the catalytic subunit from intracellular degradation.

In some embodiments, the novel chimeric polypeptides comprise a PRAD peptide. PRAD-containing ColQ was found to be necessary for AChE assembly and increasing the absolute amount of AChE expression. Expression of the AChE catalytic subunit alone results in the appearance of monomeric, dimeric and occasionally small amounts of tetrameric forms of the enzyme (FIG. 3; see reviews by Massoulié et al. 1993; Legay, 2000; Rotundo, 2003). Work from several labs has shown that co-expression of the catalytic subunits with the ColQ results in the appearance of the collagen-tailed forms. Thus the ColQ subunit alone with its PRAD containing domain is capable of inducing more complex oligomerization of AChE. As part of a study on the role of ColQ subunits in AChE assembly and post-translational regulation, tissue cultured quail QT7 skeletal muscle cells were transfected with a construct expressing chicken AChE with or without co-transfection with a cloned quail ColQ subunit. Expression of avian AChE alone results in the appearance of monomeric and dimeric AChE forms, whereas co-transfection with the ColQ results in the additional appearance of the tetrameric and collagen-tailed forms. Most importantly, co-transfection with the PRAD-containing ColQ results in a very large increase in total AChE activity. This was confirmed in experiments where shRNAs were developed to specifically target and knockdown the ColQ transcript (FIG. 3, bottom four panels). When ColQ mRNA translation was knocked down, there was a dramatic decrease in the total AChE expression. These studies not only indicate that the PRAD-containing ColQ subunit is necessary for AChE assembly, but also that it is responsible for increasing the absolute amount of AChE expression.

Recombinant cloning and expression of PRAD-containing polypeptides were performed according to methods well known to the skilled artisan and as described, for example, in Sambrook et al., *Molecular Cloning: A Laboratory Manual*, Cold Springs Harbor Laboratory, $2^{nd}$ ed., Cold Springs Harbor, N.Y. (1989). Other references describing molecular biology and recombinant DNA techniques include, for example, *DNA Cloning 1: Core Techniques*, (D. N. Glover, et al., eds., IRL Press, 1995); *DNA Cloning 2: Expression Systems*, (B. D. Hames, et al., eds., IRL Press, 1995); *DNA Cloning 3: A Practical Approach*, (D. N. Glover, et al., eds., IRL Press, 1995); *DNA Cloning 4: Mammalian Systems*, (D. N. Glover, et al., eds., IRL Press, 1995); *Oligonucleotide Synthesis* (M. J. Gait, ed., IRL Press, 1992); *Nucleic Acid Hybridization: A*

*Practical Approach*, (S. J. Higgins and B. D. Hames, eds., IRL Press, 1991); *Transcription and Translation: A Practical Approach*, (S. J. Higgins & B. D. Hames, eds., IRL Press, 1996); R. I. Freshney, *Culture of Animal Cells: A Manual of Basic Technique*, 4$^{th}$ Edition (Wiley-Liss, 1986); and B. Perbal, *A Practical Guide To Molecular Cloning*, 2$^{nd}$ Edition, (John Wiley & Sons, 1988); and *Current Protocols in Molecular Biology* (Ausubel et al., eds., John Wiley & Sons), which is regularly and periodically updated.

Chimeric polypeptides of the invention were synthesized and purified using commercially available procedures. The chimeric polypeptides can be tested in any cultured host cells expressing AChE, including host cells of different cell types and from species, such as human, mouse, or bird (e.g. quail). Non-limiting examples of preferred host cells suitable for testing the novel peptides of the invention include primary skeletal muscle cells, COS cells, HEK-293, C2/C12, and QM7 cells. Tissue culture techniques and choice of host cells are within the purview of the skilled artisan.

The peptides that exhibit the highest levels of AChE induction in the tissue culture systems will be tested for their ability to increase AChE expression in vivo. Neuromuscular junctions will be examined specifically for evidence of increased AChE accumulation. In addition, the ability of the peptides to increase serum AChE levels will also be studied with peptide antibodies.

Antibodies to the novel polypeptides of the invention may be polyclonal antibodies and may be obtained by procedures which are well known to the skilled artisan, including injecting purified wild-type AChE into various animals and isolating the antibodies produced in the blood serum. The antibodies may be monoclonal antibodies whose method of production is well known to the art, including, for example, injecting purified wild-type AChE into a mouse, isolating the spleen cells producing the anti-serum, fusing the cells with tumor cells to form hybridomas and screening the hybridomas. Once the antibody is provided, the levels of polypeptide present in vivo can be detected and/or quantitated.

The polypeptides provided herein can be formulated into pharmaceutical compositions by admixture with pharmaceutically acceptable nontoxic excipients and carriers. The formulations of the invention are useful for parenteral administration, for example, intravenous, subcutaneous, intramuscular, intraventricular, intracranial, intracapsular, intraspinal, intracisternal, or intraperitoneal administration. In accordance with the invention, the preferred routes of administration are intravenous, intramuscular, and subcutaneous. The compositions can be formulated for parenteral administration to humans or other animals in therapeutically effective amounts (e.g., amounts which eliminate or reduce the patient's pathological condition) to provide therapy for the organophosphate poisoning described above. Exemplary formulations include aqueous solutions or lyophilized powders for dilution.

The compositions may conveniently be administered in unit dosage form and may be prepared by any of the methods well known in the pharmaceutical art, for example, as described in Remington's Pharmaceutical Sciences. Formulations for parenteral administration may contain as common excipients sterile water or saline, polyalkylene glycols such as polyethylene glycol, and the like. In particular, biocompatible, biodegradable lactide polymer, lactide/glycolide copolymer, or polyoxyethylene-polyoxypropylene copolymers may be useful excipients to control the release of the proteins. Other potentially useful parenteral delivery systems for the chimeric proteins include ethylene-vinyl acetate copolymer particles, osmotic pumps, implantable infusion systems, and liposomes.

The concentration of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges would be from about 1 μg/kg to about 10 mg/kg of body weight per day; a preferred dose range is from about 0.01 mg/kg to 1 mg/kg of body weight per day.

Thus, chimeric polypeptides of the invention will be useful for administration to humans suffering from organophosphate poisoning characterized by inactivated acetylcholinesterase, as described above. When administered to a human, these novel polypeptides will effectively neutralize organophosphate poisoning by enhancing endogenous AChE expression.

While the invention has been described in terms of peptides and methods useful for the treatment of organophosphate exposure, the invention will also be useful for the design of peptides and methods useful for the treatment of other protein folding and/or degradation disorders. The concept of designing polypeptides derived from original amino acid sequences of a target molecule, that would interfere with the process of recognition involved in intracellular degradation and rescue the a protein from degradation, can apply to the treatment of any disorder which involves problems with protein folding and/or degradation. Such disorders include, but are not limited to, Alzheimer's disease, Parkinson's disease, Huntington's disease, and cystic fibrosis.

Reference will now be made to specific examples illustrating the constructs and methods above. It is to be understood that the examples are provided to illustrate preferred embodiments and that no limitation to the scope of the invention is intended thereby.

EXAMPLES

Example 1

Co-Expression of the Cloned ColQ PRAD can Enhance AChE Expression

While developing a method for targeting AChE to the apical domain of polarized cells a construct consisting of the PRAD encoding N-terminal domain of ColQ (Qn) linked to the C-terminal domain of the GPI-anchored AChE form (Duval et al., 1992) was tested. This construct, in an expression vector, encodes a chimeric protein that can associate with $AChE_t$ and anchor it to the plasma membrane via the glycophosphoinositol moiety. When co-expressed with the rat AChEt subunit the enzyme was targeted to the apical domain of polarized epithelial cells, as predicted, but in addition resulted in a very large increase in AChE activity (FIG. 4). In some cells, such as the murine NIH-3T3 cell line, the effects of the PRAD can be even more pronounced (FIG. 5). This is not simply due to increased retention as in the absence of the GPI anchor there is still a large increase in secreted tetramers (see next Example).

Example 2

Synthetic ColQ PRAD Peptides Alone can Enhance AChE Expression

Figure 6:
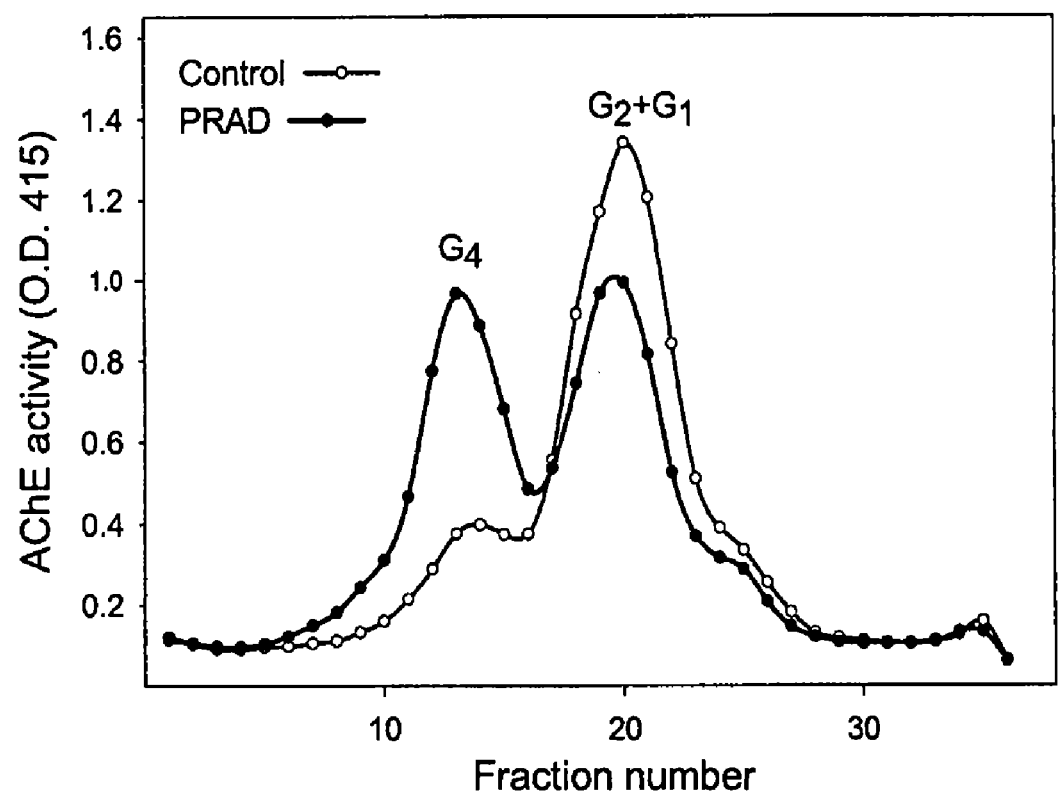
FIG. 6 illustrates the incubation of primary quail muscle cells in culture with the ColQ PRAD peptide. Muscle cultures were incubated overnight in defined medium with or without 10 uM ColQ PRAD. The next day aliquots of the medium were analyzed by velocity sedimentation and the fractions assayed for AChE. The presence of the simple ColQ PRAD alone results in a more than doubling of the tetrameric G4 AChE activity.

Since co-expression of the several PRAD-containing constructs with AChE catalytic subunits resulted in the appearance of additional AChE activity, the PRAD peptide alone was tested for similar activity. The 17 amino acid ColQ PRAD polypeptide (SEQ ID NO:1) was commercially synthesized and purified. Incubation of several different cell types including primary skeletal muscle cells, COS cells and HEK-293 cells expressing AChE from several species all showed increased AChE expression in the presence of the ColQ PRAD peptide (FIG. 6).

A modified ColQ PRAD peptide was then developed that could be specifically targeted to the endoplasmic reticulum where the AChE molecules are vectorially discharged into the lumen co-translationally and locally assembled into multimers. A ColQ PRAD peptide was synthesized with an additional four amino acid KDEL (SEQ ID NO:3) sequence, the RER (rough endoplasmic reticulum) localization signal peptide, at the carboxyl terminus. The modified 21 amino acid sequence was thus CCLLTPPPPPLFPPPFFKDEL (SEQ ID NO:4). A companion peptide was synthesized with two additional lysine residues at the amino terminus for subsequent conjugation with fluorophores for intracellular tracking of the peptide. Its sequence is KKCCLLTPPPPPLFPPPFFKDEL (SEQ ID NO:5).

Example 3

A Synthetic ColQ PRAD Peptide with a KDEL Sequence Localizes to the Rough Endoplasmic Reticulum To determine whether the ColQ PRAD-KDEL peptide was being taken up by the cells and transported back to the endoplasmic reticulum as predicted, the companion peptide was labeled with the two lysine residues at the amino-terminus with Alexa-488 fluorophore. This fluorophore is very stable and photobleaches far less rapidly than fluorescein, Oregon Green and all other dyes in that wavelength range. Since the peptide has only one fluorophore per molecule, whereas the average secondary antibody molecule used for double labeling has 7-14 fluorophores conjugated, the difference in fluorescence intensities will be well over an order of magnitude and hence the need for a very stable dye.

Figure 7:
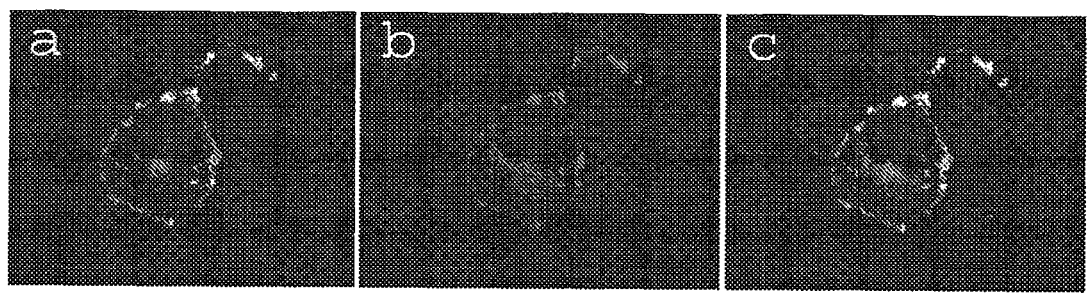
FIG. 7 illustrates the subcellular distribution of the fluorescent ColQ PRAD-KDEL peptide in COS cells. COS cells grown on laminin-coated glass coverslips were incubated for 6 hours with 10 uM Alexa-488 ColQ PRAD-KDEL peptide (a, green). The cells were then fixed, permeabilized and stained with anti-PDI antibodies and Alexa 594 secondary antibody (b, red) to label the RER. Panel c (yellow) shows the co-localization. In all cases the ColQ PRAD-KDEL peptide co-distributes with markers for the rough endoplasmic reticulum showing that it does enter the cell and is transported back to the predicted compartment where AChE is synthesized and assembled.

COS cells were incubated for 6 hours with 10 uM Alexa 488 KK-ColQ PRAD-KDEL, rinsed, fixed with 4% paraformaldehyde and then permeabilized and co-stained with anti-protein disulfide isomerase (PDI) antibodies (FIG. 7). PDI is an RER-resident protein and an excellent marker for this organelle. Moreover, it is essential for correct AChE folding. The cells were then observed using a Leica DMR-A fluorescence microscope running with Slidebook software and images captured using a Hamamatsu Orca ERII CCD camera (FIG. 7). In all cases the fluorescent ColQ PRAD-KDEL peptide was taken up by the cells and precisely co-localized with the RER marker PDI. These experiments show that the synthetic ColQ PRAD peptide is taken up by the cells and transported back to the endoplasmic reticulum where it can interact with the newly-synthesized AChE subunits to induce tetramerization and presumably prevent degradation.

Example 4

Figure 8:
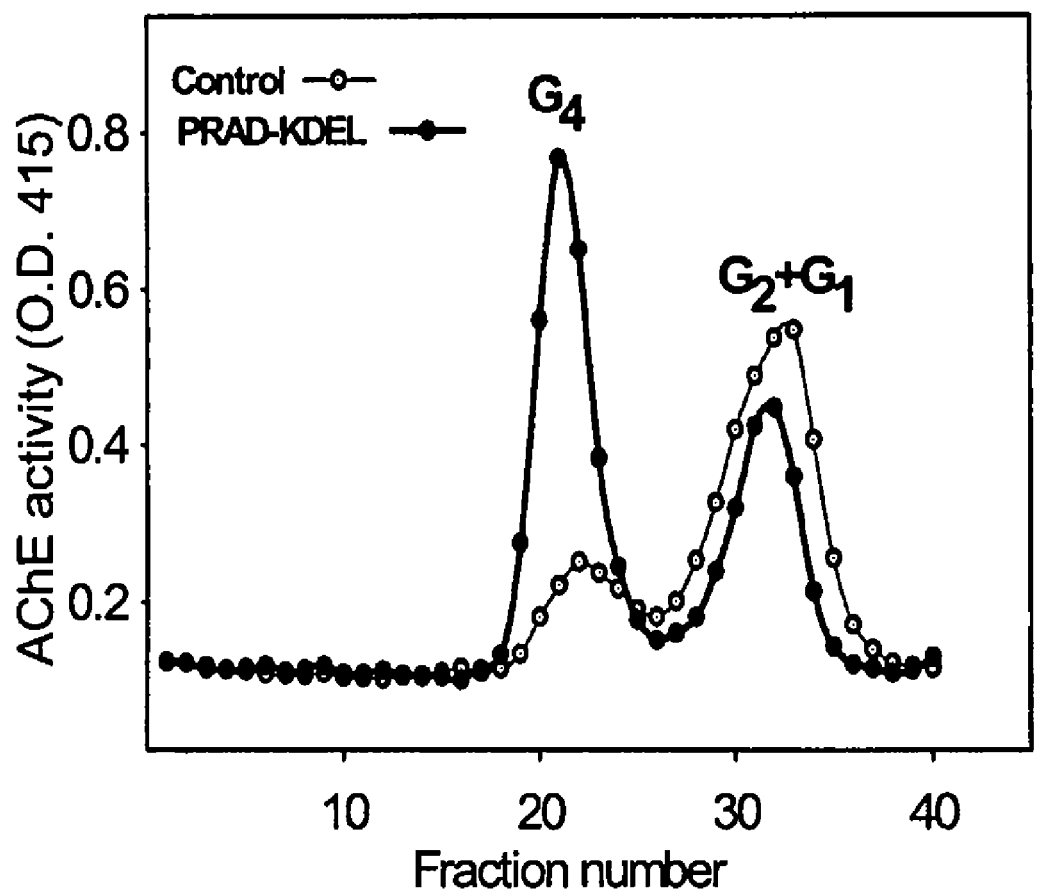
FIG. 8 illustrates the distribution of AChE forms secreted by COS cells after DFP treatment. COS cells expressing human AChE were treated with DFP and incubated in defined medium with or without 10 uM ColQ PRAD-KDEL peptide for 6 hours. The medium was then analyzed by velocity sedimentation followed by assay for AChE enzyme activity. The presence of the ColQ PRAD-KDEL peptide resulted in a 350% increase in the secreted tetrameric form of the enzyme following inactivation by an irreversible organophosphate AChE inhibitor.

The ColQ PRAD Peptide Enhances AChE Recovery from Irreversible Inactivation by Organophosphates To further test the hypothesis that the ColQ PRAD-KDEL peptide was being transported back to the RER and affecting the newly-synthesized AChE and to determine whether the peptide could also enhance the recovery of AChE from irreversible inactivation, an approach using recovery from diisopropylfluorophosphate (DFP) treatment (Rotundo, 1984; Fernandez-Valle and Rotundo, 1989; Rossi and Rotundo, 1996; Rossi et al., 2000) was used. DFP is a commercially available organophosphate compound htat behaves like the nerve gases, but is slower acting. COS cells were treated with 10 uM DFP for 10 minutes to irreversibly inhibit all cell-associated AChE and allowed to recover in defined medium in the presence or absence of 10 uM ColQ PRAD-KDEL peptide for 6 hours. Aliquots of the medium were then analyzed by velocity sedimentation and the fractions assayed for AChE activity using the method of Ellman (Ellman, et al., 1961) (FIG. 8). While there was only a small decrease in the dimeric AChE form, there was a very large 350% increase in the amount of secreted tetramer in the presence of the ColQ PRAD-KDEL peptide. These studies show that the ColQ PRAD peptide can enter the cells and increase tetrameric AChE expression several fold following irreversible inactivation of the enzyme by organophosphates.

Example 5

Determination of How the ColQ PRAD Sub-Domain of Non-catalytic AChE Subunit Increases Enzyme Expression by Rescuing Catalytic Subunits from Degradation A. Determination of Optimal Concentration of the ColQ PRAD and ColQ PRAD-KDEL Peptides for Inducing AChE Oligomerization COS cells and HEK293 cells are grown in Dulbecco's high glucose medium with 10% fetal bovine serum (FBS) and Penn-Strep. Stable cells lines expressing avian and mouse AChE were also developed, and transient transfections is also used in some experiments. A random 17 amino acid long proline-rich peptide with a KDEL sequence at the carboxyl terminus is used as a control.

COS cells expressing human, mouse, rat, or chicken AChE are grown on 35 mm culture dishes. 3-4 cultures are used per time point since inter-culture variability is usually around 5% and this includes pipeting, extraction and assay errors. At time zero the medium will be replaced with 1 ml complete medium without (control) or with the indicated peptide at concentrations ranging from 1 nM to 1 mM in 1 order of magnitude increments, and the cells incubated for 6 hours, a time which is known to be effective. The cultures are washed with Hank's Balanced Salt Solution pH 7.4 (HBSS) and the cells extracted in our standard borate extraction buffer consisting of 20 mM Borate, pH 9.0, 150 mM NaCl, 1% TX-100, 1 mM EDTA, 0.5% BSA and a protease inhibitor cocktail (Borate extraction buffer) at 500 ul/dish. After centrifugation in a microfuge 50 ul aliquots will be assayed for AChE activity using the colorimetric method of Ellman (Ellman et al., 1961). In addition, 200 ul aliquots will be analyzed by velocity sedimentation on linear 5-20% sucrose gradients in borate extraction buffer without BSA and protease inhibitor using a Beckman SW41 rotor (Rotundo, 1984; 1988).

After the initial broad range effective concentration curve is established the study is repeated with additional points over the critical range of concentrations. These studies are repeated for mouse and human AChE as necessary to establish the minimum peptide concentration that gives close to maximal expression.

B. Determination of Lag Time Between Administration of ColQ PRAD-KDEL Peptide and Oligomerization of AChE COS cells expressing human or mouse AChE are prepared as described with 3-4 cultures per time point. At time $t_0$ the cultures are rinsed twice with complete medium minus FBS but with 1.0% BSA added (defined medium) to remove serum esterases and incubated in 1 ml/dish defined medium with or without the ColQ PRAD-KDEL peptide at the optimal concentration. Time points are taken at 15 minute intervals during the first hour, 30 minute intervals during the next three hours, then at hourly intervals during the next two hours since we already know we can detect increased expression at 6 hours. At each time interval three cultures are extracted as described above and the samples held on ice until the end of the experiment at which time all samples are centrifuged and aliquots of the supernatants assayed. Samples taken at hourly intervals are analyzed by velocity sedimentation to determine the onset of oligomerization, then additional samples at the shorter time intervals are run to determine more precisely the time of onset of oligomerization.

C. Quantification of the Size and Half-Life of the Catalytically Active and Inactive AChE Pools, and Measurement of the Rates of AChE Synthesis and Maturation in the Presence or Absence of ColQ PRAD-KDEL The rate of AChE synthesis is measured using incorporation of $^{35}$S-methionine into immunoprecipitable AChE. Briefly, 60 mm cultures of COS cells expressing human AChE are incubated in methionine-free defined Dulbecco's medium with or without ColQ PRAD-KDEL containing 250 uCi/ml $^{35}$S-methionine for three hours. At 30 minute intervals two culture dishes are rinsed with HBSS, extracted with 1 ml borate extraction buffer per dish, and microfuged at 14,000×g for 20 minutes. The supernatants are diluted to 4 ml with borate extraction buffer and the AChE immunoprecipitated and analyzed by SDS gel electrophoresis as previously described (Rotundo, 1888; Rotundo et al., 1989; Fernandez-Valle and Rotundo, 1989). The gels are vacuum dried on paper and the radioactivity incorporated measured using a Phosphorimager. The experiments are repeated using a pulse-chase experimental design to determine the half-life of any rapidly turning over intracellular pool of AChE. Then, the size of the intracellular pools of active and inactive AChE is measured using techniques described previously (Rotundo, 1988). Briefly, cultures are treated with DFP to irreversibly inhibit all AChE activity and allowed to recover in defined Dulbecco's methionine-free medium containing 250 uCi/ml $^{35}$S-methionine in the presence or absence of ColQ PRAD-KDEL for two hours at which time the cultures are washed, the cells extracted in 200 ul/dish 2× borate extraction buffer. After centrifugation the samples are loaded on 5-20% sucrose gradients and the AChE forms separated by velocity sedimentation followed by fractionation of the gradients into 16 fractions (half the usual number) and the AChE activity assayed as well as the labeled protein immunoprecipitated from each fraction and analyzed by SDS gel electrophoresis and quantified. Since the tetrameric AChE is always fully active, that enzyme activity peak is used to normalize the $^{35}$S-methionine incorporation into AChE. The distribution of radioactivity and catalytically active AChE in the monomeric and dimeric regions of the gradients is compared. Differences indicate the presence of inactive enzyme molecules, and the ratios of those peaks are used to estimate the sizes of their respective pools. Our quantitative approach allows us to estimate the relative amounts of AChE that are being rescued and estimate the potential percent increase in intracellular enzyme when the ColQ PRAD-KDEL peptide is administered.

D. Production of Monoclonal Antibodies Against the 17 Amino Acid PRAD Core Peptide For in vivo studies it is necessary to have anti-PRAD antibodies to quantify the levels of peptide present in the serum at different times after administration. These are studies designed to determine the half-life of the peptides in the circulation and estimate the duration of the effects.

Example 6

Optimization of the Synthetic Peptides Designed to Rescue AChE for their Cellular Uptake and Retention as Well as their Ability to Induce Tetramerization and Increased Enzyme Stability A. Testing of Additional Peptides with Longer Amino Acid Sequence at the N- and C-Termini of the ColQ PRAD Additional ColQ PRAD-based peptides incorporating additional sequences at the amino and carboxyl ends of the peptide based upon the sequence of the human ColQ and the sequence of a mouse ColQ clone were synthesized. These sequences are as follows:

| | |
|---|---|
| VNKCCLLTPPPPPLFPPPFFKDEL | (SEQ ID NO: 6) |
| CCLLTPPPPPLFPPPFFTETKDEL | (SEQ ID NO: 7) |
| VNKCCLLTPPPPPLFPPPFFTETKDEL | (SEQ ID NO: 8) |
| KRSVNKCCLLTPPPPPLFPPPFFKDEL | (SEQ ID NO: 9) |
| CCLLTPPPPPLFPPPFFTETNILKDEL | (SEQ ID NO: 10) |
| KRSVNKCCLLTPPPPPLFPPPFFTETNILKDEL | (SEQ ID NO: 11) |

The peptides were synthesized and purified by Sigma-Genosys. The peptides were tested for solubility and then assayed for their ability to enhance AChE expression using COS cells expressing human and/or mouse AChE. Three cultures for each group were incubated with 1 ml defined medium containing the peptides at the optimal concentration determined for the original ColQ PRAD-KDEL sequence (Example 5A). The peptides' ability to increase AChE expression relative to the original ColQ PRAD-KDEL sequence was compared (Table 1). Additional studies are performed to determine what fraction of the newly-synthesized AChE peptides can convert to the tetrameric form.

TABLE 1

| PEPTIDE | G4 AChE level |
|---|---|
| Untreated control | 0.4798 |
| SEQ ID NO: 4 | 2.3748 |
| SEQ ID NO: 6 | 2.2609 |
| SEQ ID NO: 8 | 2.1710 |
| SEQ ID NO: 9 | 2.3723 |
| SEQ ID NO: 11 | 2.1384 |

B. Testing Peptides for Potential Proteolytic Cleavage

Because of the large number of basic and aromatic amino acids in the ColQ PRAD peptides, there is a large potential for proteolysis, both in culture and in vivo. Preliminary tests of proteolysis in the tissue culture system are performed before testing these peptides in vivo because rapid degradation could be interpreted as a negative effect in the in vivo experiments. (KRSVNKCCLLTPPPPPLFPPPFFTETNILKDEL: Underlined residues are potential tryptic and chymotryptic cleavage sites. There are also several potential pepsin cleavage sites in this sequence.)

The peptides are biotinylated for testing using N-hydroxy succinimide-LC-biotin (Pierce Chemical Company) and the biotinylated peptides are separated from the unreacted biotin using BioGel P2 spin columns (exclusion limit about 1,800). The peptides are conjugated at a 1:1 molar ratio to favor mono-conjugations. The biotinylated c. 2,500-3,500 kDa peptides are then be analyzed by gel-electrophoresis in 15% gels, transferred to nitrocellulose paper and blotted with alkaline phosphatase conjugated streptavidin. For these experiments the peptides are incubated with complete or serum-free defined medium to test for protease activity there. Also, the biotinylated peptides are fed to tissue-cultures cells for up to 6 hours and recovered using streptavidin-agarose beads for analysis by gel electrophoresis and blotting. If proteolytic activity is detected, a time course of proteolysis is carried out to determine the extent of the problem. If the problem is serious, the digested peptides is sent out for MADDI-TOF analysis to determine where the cleavage site occurs. A new peptide with an appropriate amino acid substitution is synthesized to remove the cleavage site.

Example 7

Initial Testing of Peptides for their Ability to Increase Tissue AChE In Vivo

Groups of six adult male mice (about 30 grams) are injected with the indicated dose of the chosen peptides and by the indicated route. 6-24 hours later the animals are sacrificed by $CO_2$ inhalation, the blood collected for assay, and the various muscle and nerve tissues removed for analysis. The tables below illustrate the design and variables for each experiment.

Serum AChE and butyrylcholinesterase (BuChE) activity: Blood collected at the time of sacrifice is allowed to coagulate at room temperature, centrifuged, and the serum transferred to microfuged tubes and frozen. For assay, 20 μl aliquots of serum are assayed using the Ellman method with either acetylthiocholine or butyrylthiocholine as substrate in the presence or absence of BW284c57 to specifically inhibit AChE activity or iso-OMPA to inhibit butyrylcholinesterase. Serum levels of each enzyme are compared to random peptide treated controls.

Tissue AChE levels: The tissues that are assayed are 1) several fast and slow muscle including the EDL, soleus, gastrocnemius and plantaris; 2) two peripheral ganglia, the superior cervical ganglion and one sensory ganglion; and 3) spinal chord and whole brain. The tissues are removed, weighed, and snap frozen in small test tubes. For assay the samples are thawed in 10 volumes borate extraction buffer, homogenized with a small Teflon homogenizer, and centrifuged. For enzyme assay a radiometric AChE assay (Johnson and Russell, 1975) is used because it is more sensitive than the colorimetric one. Briefly, 5-10 μl aliquots of tissue sample are incubated in a total volume of 25 μl 100 mM phosphate buffer, pH 7.4, with 1 mM acetylcholine containing 3H-ACh. The radioactive acetic acid produced is counted using a 2-phase scintillation cocktail that only extracts the acid. Activity is recorded either as CPM/sample/hour or as nM product/min. While most samples have ample enzyme activity, it may be necessary to pool the peripheral ganglia if insufficient activity is obtained with single samples. The basic experimental design for all the studies is given below. Each experiment is repeated.

A. Initial Testing of Peptide Concentration

Dose refers to concentration of peptide in the serum to compare with the effective concentrations observed in the in vitro studies. "n" indicates the number of mice used in each experimental group.

| Peptide dose | Control peptide | Peptide #1 | Peptide #2 | Peptide #3 | |
|---|---|---|---|---|---|
| 10 uM | N = 6 | N = 6 | N = 6 | N = 6 | Total = 24 |
| 50 uM | N = 6 | N = 6 | N = 6 | N = 6 | Total = 24 |
| 250 uM | N = 6 | N = 6 | N = 6 | N = 6 | Total = 24 |

Experiment total = 72

B. Initial Testing of Time Course of Peptide Effects

| Time after administration | Control peptide | Peptide #1 | Peptide #2 | Peptide #3 | |
|---|---|---|---|---|---|
| 6 hours | N = 6 | N = 6 | N = 6 | N = 6 | Total = 24 |
| 12 hours | N = 6 | N = 6 | N = 6 | N = 6 | Total = 24 |
| 24 hours | N = 6 | N = 6 | N = 6 | N = 6 | Total = 24 |

Experiment total = 72

C. Initial Testing of Peptide Administration Route

| Route of administration | Control peptide | Peptide #1 | Peptide #2 | Peptide #3 | |
|---|---|---|---|---|---|
| Intramuscular | N = 6 | N = 6 | N = 6 | N = 6 | Total = 24 |
| Intraperitoneal | N = 6 | N = 6 | N = 6 | N = 6 | Total = 24 |
| Subcutaneous | N = 6 | N = 6 | N = 6 | N = 6 | Total = 24 |
| Intravenous | N = 6 | N = 6 | N = 6 | N = 6 | Total = 24 |

Experiment total = 98

D. AChE Expression at the Neuromuscular Junctions of Peptide Treated Mice

Mice are injected with the optimized dose by the optimal route and the tissues removed 6-24 hours later. The muscles are dissected and bundles of fibers teased apart and stained using Alexa-488 Fasciculin 2 that specifically labels AChE (see for example, Peng et al., 1999) and Alexa 546 α-bungarotoxin (α-Btx) to label the nicotinic acetylcholine receptors (AChR). The fluorescence from 30-50 neuromuscular junctions per animal is imaged and the fluorescence of both AChE and AChR recorded and quantified using our imaging software (Adams et al., 2000). Since Fasciculin 2 binds specifically and quantitatively to AChE, any changes in absolute or relative fluorescence levels indicate changes in numbers of AChE molecules. An increase in the numbers of AChE molecules at the synapses by peptide treatments is detected as an increase in total AChE fasciculin 2 fluorescence.

| | Control peptide | Peptide #1 | Peptide #2 | Peptide #3 | |
|---|---|---|---|---|---|
| Optimal time and dose TBA | N = 6 | N = 6 | N = 6 | N = 6 | Total = 24 |

Experiment total = 24

E. Tissue Distribution of the Fluorescent Peptides Following Injection

Fluorescent peptides are produced as described previously by conjugation to Alexa 488. The purified peptides are injected into mice following the optimized protocol. At the optimal time interval the mice are sacrificed using $CO_2$ and the listed tissues removed, rinsed, and fixed in 4% buffered paraformaldehyde overnight. The tissues are snap frozen and 10 um sections cut in a cryostat and mounted on glass slides. After a second fixation the slides are rinsed and mounted. The tissues are viewed using our Leica DMR-A fluorescence microscope and imaged using Metamorph software.

Example 8

Determination of the Ability of the Synthetic Peptides to Protect Mice from Exposure to Organophosphate Nerve Agents and their Ability to Improve Survival when Administered After Exposure A. Determination of the Ability of the PRAD-KDEL Peptides to Protect Mice from DFP Administration Published values for the LD50 of DFP in mice depend in part on the strain (Smolen et al., 1985; Tripathi and Dewey, 1989) but are similar enough that 7 mg/kg is used as a starting point for a dose response curve. Mice are first injected with an optimal dose of the selected PRAD-KDEL peptide or the random KDEL peptide control at a time before DFP injection. Mice are then injected with DFP intraperitonealy at doses of 0.25, 0.50, 1.0, 2.0, 5.0 and 10.0 times the LD50 of 7 mg/kg. The DFP is purchased from Sigma-Aldrich Chemical Company and does not require special containment beyond the usual safety precautions of working in a chemical fume hood and being careful with decontamination of all the glass and plasticware. The animals are kept under continuous observation during the next 24 hours to record their behaviors and determine the occurrence and time of death. This experiment is repeated once with these DFP doses, and then an additional two times with the modified dose range to be decided upon completion of the first set of studies as the doses may need to be changed up or down.

| | Control peptide | Peptide #1 | Peptide #2 | Peptide #3 | |
|---|---|---|---|---|---|
| 0.25 $LD_{50}$ DFP | N = 6 | N = 6 | N = 6 | N = 6 | Total = 24 |
| 0.50 $LD_{50}$ DFP | N = 6 | N = 6 | N = 6 | N = 6 | Total = 24 |
| 1.00 $LD_{50}$ DFP | N = 6 | N = 6 | N = 6 | N = 6 | Total = 24 |
| 2.00 $LD_{50}$ DFP | N = 6 | N = 6 | N = 6 | N = 6 | Total = 24 |
| 5.00 $LD_{50}$ DFP | N = 6 | N = 6 | N = 6 | N = 6 | Total = 24 |
| 10.0 $LD_{50}$ DFP | N = 6 | N = 6 | N = 6 | N = 6 | Total = 24 |

Experiment total = 144

B. Estimation of the Half-Life of the Peptides in the Circulation

Mice are injected with a high functional dose of the two most effective peptides and four animals from each group are sacrificed at the indicated times. Blood is drawn and the serum concentrations of the peptide assayed by an enzyme-linked immunoassay. This experiment is repeated once, but the possibility to change the temporal parameters depending on the observed half-life in the first study is left open.

| Time after injection | Peptide #1 | Peptide #2 | |
|---|---|---|---|
| 0 | N = 4 | N = 4 | Total = 8 |
| 3 hrs | N = 4 | N = 4 | Total = 8 |
| 6 hrs | N = 4 | N = 4 | Total = 8 |
| 12 hrs | N = 4 | N = 4 | Total = 8 |
| 24 hrs | N = 4 | N = 4 | Total = 8 |

Experiment total = 40

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. In addition, all references cited herein are indicative of the level of skill in the art and are hereby incorporated by reference in their entirety.

REFERENCES

Adams, M. E., N. R. Kramarcy, S. P. Krall, S. G. Rossi, R. L. Rotundo, R. Sealock, and S. C. Froehner. 2000. *J. Cell Biol.* 150(6):1385-1397.

Bon, S., F. Coussen, and J. Massoulié. 1978. *The Journal of Bio. Chem.* 272(5): 3016-3021.

Bon, S, and J. Massoulie. 1997. *The Journal of Bio. Chem.* 272(5):3007-3015.

Chitlaru, T., C. Kronman, B. Velan, and A. Shafferman. 2001. *Biochemical Journal* 354: 613-625.

Duval, N., E. Krejci, J. Grassi, F. Coussen, J. Massoulie, and S. Bon. 1992. *The EMBO Journal* 11(9):3255-3261.

Dvir H., M. Harel, S. Bon, W. Q. Liu, M. Vidal, C. Garbay, J. L. Sussman, J. Massoulié, and I. Silman, 2004. *EMBO J.* 23:4394-2405.

Ellman, G. L., K. D. Courtney, V. Andres Jr., and R. M. Featherstone. 1961. *Biochem Pharmacol.* 7:88-95.

Fernandez-Valle, C. and R. L. Rotundo. 1989. *J. Biol. Chem.* 264, 14043-14049.

Johnson C. D. and R. L. Russell. 1975. *Anal Biochem.* 64:229-238.

Kimbell, K. M., K. Ohno, A. G. Engel, and R. L. Rotundo. 2003. *J. Biol. Chem.*

Legay, C. 2000. *Microsc. Res. Tech.* 49: 56-72.

Legay, C., F. A. Mankal, J. Massoulié and B. J. Jasmin. 1999. *J. Neuroscience* 19: 8251-8259.

Massoulié, J., L. Pezzementi, S. Bon, E. Krejci, and F. M. Vallette. 1993. *Prog. Neurobiol.* 41: 31-91.

Peng, B. H., H. Xie, S. G. Rossi, and R. L. Rotundo. 1999. *The Journal of Cell Biology* 145:911-921

Rossi, S. G. and R. L. Rotundo. 1996. *J. Biol. Chem.* 271: 1979-1987.

Rossi, S. G., A. E. Vazquez, and R. L. Rotundo. 2000. *J. Neurosci.* 20:919-928.

Rotundo, R. L. 1984. *Proc. Natl. Acad. Sci. USA* 81:479-483.

Rotundo, R. L. 1988. *J. Biol. Chem.* 263:19398-19406.

Rotundo, R. L., K. Thomas, K. Porter-Jordan, R. J. J. Benson, C. Fernandez-Valle, and R. E. Fine. 1989. *J. Biol. Chem.* 264(6):3146-3152.

Saxena, A., L. Raveh, Y. Ashani, and B. P. Doctor. 1997. *Biochem.* 36:7481-7489.

Saxena, A., Y. Ashani, L. Raveh, D. Stevenson, T. Patel, and B. P. Doctor. 1998. *Molecular Pharmacology* 53:112-122.

Smolen, A., T. N. Smolen, J. M. Wehner and A. C. Collins. 1985. *Pharmacol. Biochem. Behav.* 22: 623-630.

Tripathi, H. L. and Dewey, W. L. 1985. *J. Toxicology and Environmental Health* 26: 437-446.

What is claimed is:

1. A chimeric polypeptide comprising an amino acid sequence selected from the group consisting of SEQ ID NO:2, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

2. The chimeric polypeptide according to claim 1, wherein the polypeptide is derived from acetylcholinesterase collagenic tail peptide.

3. The chimeric polypeptide according to claim 1, wherein the polypeptide has an amino acid sequence comprising SEQ ID NO:2.

4. The chimeric polypeptide according to claim 1, further comprising an endoplasmic retention signal.

5. The chimeric polypeptide according to claim 4, wherein the endoplasmic retention signal has an amino acid sequence comprising SEQ ID NO:3.

6. The chimeric polypeptide according to claim 1, further comprising a signal for conjugating a label, wherein the label is fluorescent.

7. A pharmaceutical composition comprising a chimeric polypeptide and a pharmaceutically acceptable carrier, excipient, or diluent, wherein the chimeric polypeptide enhances endogenous acetylcholinesterase expression, the chimeric polypeptide comprising an amino acid sequence selected from the group consisting of SEQ ID NO:2, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

8. A method of treating an animal exposed to an organophosphate comprising administering to the animal a therapeutically effective amount of a chimeric polypeptide, wherein the chimeric polypeptide enhances, endogenous acetylcholinesterase expression, the chimeric polypeptide comprising an amino acid sequence selected from the group consisting of SEQ ID NO: 1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

9. The method of claim 8, wherein the therapeutically effective amount of the chimeric polypeptide is administered parenterally, intramuscularly, intraperitoneally, subcutaneously, or intravenously.

10. The method of claim 8, wherein the therapeutically effective amount of the chimeric polypeptide is administered in a dose range from about 0.1 mg/kg to about 10 mg/kg of body weight per day.

11. A method of treating an animal exposed to an organophosphate comprising administering to the animal a therapeutically effective amount of a pharmaceutical composition comprising a chimeric polypeptide wherein the chimeric polypeptide enhances endogenous acetylcholinesterase expression, the chimeric polypeptide comprising an amino acid sequence selected from the group consisting of SEQ ID NO: 1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

12. The method of claim 11, wherein the therapeutically effective amount of the pharmaceutical composition is administered parenterally, intramuscularly, intraperitoneally, subcutaneously, or intravenously.

13. The method of claim 11, wherein the therapeutically effective amount of the pharmaceutical composition is administered in a dose range from about 0.1 mg/kg to about 10 mg/kg of body weight per day.

14. The method of claim 10 or 11, wherein the organophosphate is a nerve gas.

15. The method of claim 14, wherein the nerve gas is selected from the group consisting of sarin, soman, tabun and vx.

16. The method of claim 8 or 11, wherein the organophosphate is a pesticide.

17. The method of claim 16, wherein the pesticide is selected from the group consisting of malathion, parathion, diazinon, fenthion, dichlorvos, and chlorpyrifos.

18. A method of enhancing endogenous acetylcholinesterase expression in an animal in need thereof, comprising administering to the animal a therapeutically effective amount of a chimeric polypeptide wherein the chimeric polypeptide enhances endogenous acetylcholinesterase expression, the chimeric polypeptide comprising an amino acid sequence selected from the group consisting of SEQ ID NO: 1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, and SEC) ID NO: 11.

19. The method of claim 18, wherein the therapeutically effective amount of the chimeric polypeptide is administered parenterally, intramuscularly, intraperitoneally, subcutaneously, or intravenously.

20. The method of claim 18, wherein the therapeutically effective amount of the chimeric polypeptide is administered in a dose range from about 0.1 mg/kg to about 10 mg/kg of body weight per day.

21. A method of enhancing endogenous acetylcholinesterase expression in an animal in need thereof, comprising administering to the animal a therapeutically effective amount of a pharmaceutical composition comprising a chimeric polypeptide wherein the chimeric polypeptide enhances endogenous acetylcholinesterase expression, the chimeric polypeptide comprising an amino acid sequence selected from the group consisting of SEQ ID NO: 1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

22. The method of claim 21, wherein the therapeutically effective amount of the pharmaceutical composition is administered parenterally, intramuscularly, intraperitoneally, subcutaneously, or intravenously.

23. The method of claim 21, wherein the therapeutically effective amount of the pharmaceutical composition is administered in a dose range from about 0.1 mg/kg to about 10 mg/kg of body weight per day.

24. A kit for treating organophosphate poisoning comprising a therapeutically effective amount of a chimeric polypeptide according to claim 1.

\* \* \* \* \*

SEQUENCE LISTING

<160> NUMBER OF SEQ ID NOS: 12

<210> SEQ ID NO 1
<211> LENGTH: 17
<212> TYPE: PRT
<213> ORGANISM: Artificial Sequence
<220> FEATURE:
<223> OTHER INFORMATION: acetylcholinesterase collagenic tail peptide

<400> SEQUENCE: 1

Cys Cys Leu Leu Thr Pro Pro Pro Pro Leu Phe Pro Pro Pro Phe
1               5                   10                  15

Phe

<210> SEQ ID NO 2
<211> LENGTH: 17
<212> TYPE: PRT
<213> ORGANISM: Artificial Sequence
<220> FEATURE:
<223> OTHER INFORMATION: acetylcholinesterase transmembrane anchor
      protein

<400> SEQUENCE: 2

Arg Pro Pro Pro Pro Leu Pro Pro Pro Leu Pro Pro Pro Pro Pro
1               5                   10                  15

Arg

<210> SEQ ID NO 3
<211> LENGTH: 4
<212> TYPE: PRT
<213> ORGANISM: Artificial Sequence
<220> FEATURE:
<223> OTHER INFORMATION: endoplasmic reticulum retention signal

<400> SEQUENCE: 3

Lys Asp Glu Leu
1

<210> SEQ ID NO 4
<211> LENGTH: 21
<212> TYPE: PRT
<213> ORGANISM: Artificial sequence
<220> FEATURE:
<223> OTHER INFORMATION: novel chimeric peptides

<400> SEQUENCE: 4

Cys Cys Leu Leu Thr Pro Pro Pro Pro Leu Phe Pro Pro Pro Phe
1               5                   10                  15

Phe Lys Asp Glu Leu
            20

<210> SEQ ID NO 5
<211> LENGTH: 23
<212> TYPE: PRT
<213> ORGANISM: Artificial Sequence
<220> FEATURE:
<223> OTHER INFORMATION: novel chimeric peptides

<400> SEQUENCE: 5

Lys Lys Cys Cys Leu Leu Thr Pro Pro Pro Pro Leu Phe Pro Pro
1               5                   10                  15

Pro Phe Phe Lys Asp Glu Leu
            20

```
<210> SEQ ID NO 6
<211> LENGTH: 24
<212> TYPE: PRT
<213> ORGANISM: Artificial Sequence
<220> FEATURE:
<223> OTHER INFORMATION: novel chimeric peptides

<400> SEQUENCE: 6

Val Asn Lys Cys Cys Leu Leu Thr Pro Pro Pro Pro Leu Phe Pro
1               5                   10                  15

Pro Pro Phe Phe Lys Asp Glu Leu
            20

<210> SEQ ID NO 7
<211> LENGTH: 24
<212> TYPE: PRT
<213> ORGANISM: Artificial Sequence
<220> FEATURE:
<223> OTHER INFORMATION: novel chimeric peptides

<400> SEQUENCE: 7

Cys Cys Leu Leu Thr Pro Pro Pro Pro Leu Phe Pro Pro Pro Phe
1               5                   10                  15

Phe Thr Glu Thr Lys Asp Glu Leu
            20

<210> SEQ ID NO 8
<211> LENGTH: 27
<212> TYPE: PRT
<213> ORGANISM: Artificial Sequence
<220> FEATURE:
<223> OTHER INFORMATION: novel chimeric peptides

<400> SEQUENCE: 8

Val Asn Lys Cys Cys Leu Leu Thr Pro Pro Pro Pro Leu Phe Pro
1               5                   10                  15

Pro Pro Phe Phe Thr Glu Thr Leu Asp Glu Leu
            20                  25

<210> SEQ ID NO 9
<211> LENGTH: 27
<212> TYPE: PRT
<213> ORGANISM: Artificial Sequence
<220> FEATURE:
<223> OTHER INFORMATION: novel chimeric peptides

<400> SEQUENCE: 9

Lys Arg Ser Val Asn Lys Cys Cys Leu Leu Thr Pro Pro Pro Pro
1               5                   10                  15

Leu Phe Pro Pro Pro Phe Phe Lys Asp Glu Leu
            20                  25

<210> SEQ ID NO 10
<211> LENGTH: 27
<212> TYPE: PRT
<213> ORGANISM: Artificial sequence
<220> FEATURE:
<223> OTHER INFORMATION: novel chimeric peptides

<400> SEQUENCE: 10

Cys Cys Leu Leu Thr Pro Pro Pro Pro Leu Phe Pro Pro Pro Phe
1               5                   10                  15

Phe Thr Glu Thr Asn Ile Leu Lys Asp Glu Leu
            20                  25
```

-continued

```
<210> SEQ ID NO 11
<211> LENGTH: 33
<212> TYPE: PRT
<213> ORGANISM: Artificial sequence
<220> FEATURE:
<223> OTHER INFORMATION: novel chimeric peptides

<400> SEQUENCE: 11

Lys Arg Ser Val Asn Lys Cys Cys Leu Leu Thr Pro Pro Pro Pro Pro
1               5                   10                  15

Leu Phe Pro Pro Pro Phe Phe Thr Glu Thr Asn Ile Leu Lys Asp Glu
            20                  25                  30

Leu

<210> SEQ ID NO 12
<211> LENGTH: 21
<212> TYPE: PRT
<213> ORGANISM: Artificial sequence
<220> FEATURE:
<223> OTHER INFORMATION: novel chimeric peptides

<400> SEQUENCE: 12

Arg Pro Pro Pro Pro Leu Pro Pro Pro Pro Leu Pro Pro Pro Pro Pro
1               5                   10                  15

Arg Lys Asp Glu Leu
            20
```